(12) United States Patent
Pagani et al.

(10) Patent No.: US 6,702,992 B2
(45) Date of Patent: Mar. 9, 2004

(54) METHOD FOR MODERNIZING A UREA PRODUCTION PLANT (75) Inventors: Giorgio Pagani, Lugano (CH); Federico Zardi, Breganzona (CH)

(73) Assignee: Urea Casale S.A., Lugano-Besso (CH)

( * ) Notice: Subject to any disclaimer, the term of this patent is extended or adjusted under 35 U.S.C. 154(b) by 37 days.

(21) Appl. No.: 09/881,099

(22) Filed: Jun. 15, 2001

(65) Prior Publication Data

US 2001/0031893 A1 Oct. 18, 2001

Related U.S. Application Data (62) Division of application No. 09/527,221, filed on Mar. 16, 2000.

(30) Foreign Application Priority Data

Mar. 16, 1999 (EP) .............................................. 99200794

(51) Int. Cl.$^7$ .............................. B01J 8/04; B01J 10/00
(52) U.S. Cl. ........................... 422/189; 564/67; 564/68; 564/70; 564/71; 564/72; 422/100; 422/191; 422/192; 422/193
(58) Field of Search ............................. 564/67, 68, 70, 564/69, 71, 72; 422/189–191, 192, 193

(56) References Cited

U.S. PATENT DOCUMENTS

| 4,012,443 | A | * | 3/1977 | Bonetti | ................... 260/555 A |
|---|---|---|---|---|---|
| 5,523,483 | A | * | 6/1996 | Singh et al. | ................... 564/68 |
| 5,681,537 | A | | 10/1997 | Pagani | ......................... 422/19 |
| 5,849,952 | A | | 12/1998 | Carloni et al. | ................ 564/71 |
| 5,886,222 | A | | 3/1999 | Rescalli | ....................... 564/70 |
| 6,392,096 | B1 | * | 5/2002 | Mennen et al. | ................ 564/70 |

FOREIGN PATENT DOCUMENTS

| EP | 0 796 244 | 7/1998 |
|---|---|---|
| NL | 1 004 977 | 7/1998 |
| WO | WO 96/23767 | 8/1996 |

* cited by examiner

*Primary Examiner*—Glenn Caldarola
*Assistant Examiner*—Alexis Wachtel
(74) *Attorney, Agent, or Firm*—Sughrue Mion, PLLC (57) ABSTRACT

A method for the modernization of a plant for urea production of the type comprising a reactor (2) for urea synthesis, a stripping unit (3) with carbon dioxide and at least one vertical condensation unit (4) of the film type, foresees the provision of means (36) for feeding a major portion of a flow comprising ammonia and carbon dioxide in vapor phase leaving the stripping unit (3) to the condensation unit (4) and the provision in said condensation unit (4) of means (37) for subjecting to substantially total condensation such major portion of the flow comprising ammonia and carbon dioxide in vapour phase, obtaining a flow comprising urea and carbamate in aqueous solution, then fed to the reactor (2) for urea synthesis. Thanks to the present method of modernisation, the efficiency of the condensation unit (4) is remarkably improved, thus permitting an increase of its capacity.

14 Claims, 6 Drawing Sheets

METHOD FOR MODERNIZING A UREA PRODUCTION PLANT

This is a divisional of application Ser. No. 09/527,221 filed Mar. 16, 2000, the disclosure of which is incorporated herein by reference.

FIELD OF APPLICATION

The present invention relates to a method for the modernisation of a plant for urea production according to the process with stripping with carbon dioxide.

More specifically, the invention relates to a method for the modernisation of a plant for urea production of the type comprising:

- a reactor for urea synthesis;
- means for feeding ammonia and carbon dioxide to the reactor for urea synthesis;
- a stripping unit with carbon dioxide for subjecting a reaction mixture comprising urea, carbamate and free ammonia in aqueous solution leaving the reactor to a treatment of partial decomposition of carbamate and partial separation of free ammonia, thus obtaining a flow comprising ammonia and carbon dioxide in vapour phase and a flow comprising urea and residual carbamate in aqueous solution, respectively;
- a recovery section for the flow comprising urea and residual carbamate in aqueous solution leaving the stripping unit for separating urea from the residual carbamate in aqueous solution;
- at least one vertical condensation unit of the film type, comprising a tube bundle for subjecting to partial condensation the flow comprising ammonia and carbon dioxide in vapour phase leaving the stripping unit, thus obtaining a liquid flow comprising carbamate in aqueous solution and a gaseous flow comprising ammonia and carbon dioxide in vapour phase;
- means for respectively feeding the flow comprising carbamate in aqueous solution and the flow comprising ammonia and carbon dioxide in vapour phase to the reactor for urea synthesis;
- means for feeding a gaseous flow comprising one or more passivating agents, inert with respect to the synthesis reaction of urea, to the stripping unit and from the stripping unit to the reactor for urea synthesis through the condensation unit.

In the following description and enclosed claims, with the term "modernisation", it is intended to mean the modification of a pre-existing plant with the purpose of improving its performance and obtaining, for example, an increase of the production capacity and/or of the conversion yield as well as a reduction of the energy consumption. In particular, the modernisation of a urea plant according to the present invention foresees to increase the capacity, maintaining the main equipment of the high pressure synthesis section (synthesis loop).

In the following description and enclosed claims, with the term "condensation unit of the film type", it is intended to mean an apparatus wherein the condensation of the gaseous phase occurs in a liquid film, flowing downwards inside a plurality of tubes in co-current with the gaseous flow. The liquid film flows in contact with the tube wall whereas the gaseous phase flows inside the tubes.

According to a further aspect of thereof, the present invention also relates to a process for urea production as well as to a plant for carrying out such process.

As known, with respect to urea production, the need is more and more felt of having on one hand plants of always greater capacity and operation efficiency available, and on the other hand of having lower and lower investment and operation costs, as well as lower energy consumption.

PRIOR ART

To this end, methods for the modernisation of existing plants for urea production according to the stripping process with carbon dioxide have been recently set forth in the field, substantially based on the modification of the synthesis reactor, on the replacement of the apparatuses downstream the synthesis reactor with apparatuses of greater capacity and/or on the addition of new apparatuses in parallel to the existent apparatuses.

For example, in EP-A-0 796 244 a method of modernisation of a plant for urea production is disclosed, which foresees the addition of a partial decomposition step of the carbamate in aqueous solution recycled to the synthesis reactor. With this method of modernisation, it is possible to remarkably reduce the amount of water recycled to the synthesis reactor, thus permitting to obtain an increase of the conversion yield and therefore of the production capacity of the plant.

One of the main problems that is encountered when an increase of production capacity is considered in existing plants for urea production according to a stripping process with carbon dioxide, is that of increasing the capacity of the high pressure condensation section which may comprise one or more condensation units.

The methods of modernisation for increasing the capacity of said condensation section proposed to date always foresee the insertion in parallel of additional condensation units of the film type or of a unit provided with a high exchange coefficient, for example a horizontal condensation unit of the Kettle type (pool condenser).

In some instances the replacement of the existing unit(s) with new units of greater capacity must be even taken into account.

Such provisions have a very negative impact both on investment costs and on the constructional complexity relative to the modernisation of the condensation section according to the above mentioned methods of the prior art.

Because of these disadvantages, the modernisation of plants for urea production according to the stripping process with carbon dioxide has found to date a relatively reduced application, notwithstanding the ever increasing interest of industry of modifying the existing plants—instead of replacing them with new plants—with the purpose of increasing the production capacity and decreasing the energy costs.

SUMMARY OF THE INVENTION

The technical problem underlying the present invention is therefore that of providing a method for the modernisation of a plant for urea production which allows an increase of the production capacity thereof, implies low energy consumption and investment costs and is technically easy to be implemented.

According to the present invention, this problem is solved by a method of the aforementioned type, which is characterised by comprising the steps of:

- providing means for feeding a minor portion of the flow comprising ammonia and carbon dioxide in vapour phase together with a minor portion of the gaseous flow comprising one or more passivating agents leaving the stripping unit directly to the reactor for urea synthesis;

providing means for feeding a major portion of the flow comprising ammonia and carbon dioxide in vapour phase together with a major portion of the gaseous flow comprising one or more passivating agents leaving the stripping unit to such at least one condensation unit;

providing in such at least one condensation unit means for subjecting to substantially total condensation the major portion of the flow comprising ammonia and carbon dioxide in vapour phase, obtaining a flow comprising urea and carbamate in aqueous solution.

As far as the term major portion is concerned, this indicates a portion greater than 50% of the total flow of ammonia and carbon dioxide in vapour phase coming out of the stripping unit. Depending on the operating conditions in the synthesis reactor, the major portion can be in a range between 65 and 85% of such flow, for example between 70 and 75%.

Advantageously, the present invention permits to remarkably increase the exchange coefficient and therefore the efficiency of the condensation section, permitting a debottlenecking of the existing plant to full advantage of the overall production capacity, which may be therefore optimally increased.

All this is attained in a simple and effective way, with minimum and quite secondary interventions in the high pressure synthesis section that is thus maintained substantially unchanged, and with low energy consumption.

Accordingly the investment, implementation and operation costs are considerably lower than the costs required by the methods of modernisation according to the prior art.

In fact, thanks to the present method, the pre-existing condensation section is not upgraded nor replaced with new apparatuses, but advantageously preserved, requiring only small internal modifications of the condensation unit(s) in such a way to obtain a substantially total condensation of the gaseous phase fed therein.

Thanks to the fact of providing means for splitting respectively in a minor and major portion the flow comprising ammonia and carbon dioxide in vapour phase (coming from the stripping unit), the portion of reactants in gaseous phase necessary for controlling the reaction temperature inside the synthesis reactor is not made any longer to pass through the condensation unit together with the liquid phase, as in the prior art. So doing, the condensation unit can be modified internally in such a way to permit the substantial condensation of all the gaseous reactants comprised in the major portion and hence to operate at the maximum efficiency obtainable.

In this respect, the present method of modernisation advantageously comprises the step of providing means for transforming the vertical condensation unit of the film type in a vertical condensation unit of the "submerged" type.

In the following description and in the enclosed claims, with the term "condensation unit of the submerged type", it is intended to mean an apparatus wherein the liquid phase fills (submerges) the tube bundle and wherein the condensation of the gaseous phase occurs by passing through such liquid phase. In other words, in this case, the condensation unit operates having the tube bundle's tubes full of liquid, differently from the condensation unit of the film type wherein the tubes are substantially empty.

More in particular, the existing condensation unit is advantageously modified by providing means for feeding the major portion of the flow comprising ammonia, carbon dioxide in vapour phase in a lower end of the tube bundle of such at least one unit and means for circulating a flow of condensation liquid comprising carbamate in aqueous solution and ammonia inside the condensation unit with a thermosiphon like motion.

Thanks to the present invention, the vertical position and the dimension of the existing condensation unit are exploited, which guarantee—once transformed—a high liquid head (height) and therefore a natural circulation of the same inside the tube bundle (thermosiphon like motion).

The circulation according to a thermosiphon like motion of the liquid phase is due to the difference of specific weight between the flow comprising liquid and vapours flowing upwards in the apparatus and the flow of liquid only directed downwards through respective portions of the tube bundles.

In this respect, particularly satisfying results have been obtained providing a gas distributor proximate to the lower end of the tube bundle in fluid communication with the means for feeding the major portion of the flow comprising ammonia and carbon dioxide in vapour phase, so as to distribute the ammonia and carbon dioxide in vapour phase in a preferably central, predetermined portion of the tube bundle.

In this way, the condensation of ammonia and carbon dioxide in vapour phase is made advantageously occur only in a well defined portion of the tube bundle, thus promoting an optimal circulation in a thermosiphon like motion of the liquid phase inside the condensation unit between the portion of the tube bundle through which the low specific weight flow passes (gaseous phase mixed with the liquid phase) and the portion of tube bundle (preferably in a peripheral position) through which the high specific weight flow passes (liquid phase only).

With respect to a condensation unit of the film type, the condensation unit provided by the present method of modernisation permits an effective mixing of the gaseous phase in the liquid phase obtaining in this way a remarkable increase of the exchange coefficient inside the tubes and therefore increasing the overall exchange coefficient and the efficiency of the pre-existing condensation section.

This allows to increase the capacity of the existing condensation section.

Test results have shown that it is even possible to double the overall exchange coefficient of the existing condensation unit.

Further, thanks to the step of modifying the vertical condensation unit(s) from the film type to the "submerged" type, with thermosiphon like circulation of the liquid phase, it is possible to increase—in a simple and effective way—the residence time in such units of the therein provided carbamate, which can thus react and be partially transformed in urea.

In doing so, it is possible to obtain an increase even equal to 10–20%, of the overall reaction volume, that is of the residence time of the carbamate in the condensation unit and in the reaction space. This factor advantageously implies a corresponding increase of the conversion yield of the carbon dioxide into urea.

In order to extract from the condensation section the flow comprising carbamate in aqueous solution and urea so obtained without having to bring remarkable modifications to the original structure, the method of modernisation according to the present invention comprises advantageously the provision in the condensation unit(s) of means for collecting and feeding the aforesaid flow from an area above the tube bundle to a lower end of the condensation unit in fluid communication with the means for feeding the liquid phase to the reactor for urea synthesis.

It is important to notice how, contrary to the recurrent teaching of the prior art, that suggests to upgrade the condensation section adding new condensation units or replacing the existing one with a new unit with a high exchange coefficient, the method of modernisation according to the present invention permits to achieve the same (if not greater) capacity increases with the existing condensation unit(s), which are advantageously only slightly modified from the structural point of view but are dramatically changed as far as their operation is concerned.

This result is absolutely surprising if we consider that according to the methods of modernisation of the prior art it was not conceivable to obtain substantial capacity increases in the condensation section with the existing apparatuses only.

According to a particularly advantageous and preferred embodiment of the present invention, the present method of modernisation further comprises the step of:

providing means for extracting and feeding the major portion of the gaseous flow comprising one or more passivating agents together with possible traces of ammonia and carbon dioxide in vapour phase from such at least one condensation unit to a washing unit provided downstream the reactor for urea synthesis.

In other words, through the introduction of suitable means, the major portion of the gaseous flow comprising the passivating agents fed by the stripping unit to the condensation unit is advantageously deviated to any one of the washing units located in the plant downstream of the reaction space instead of passing through the same.

Advantageously, the method of modernisation according to the present invention permits therefore to feed to the reactor for urea synthesis only a minor portion of the gaseous slow comprising the passivating agents, thus reducing to a minimum the presence of substances extraneous to the conversion reaction—to full advantage of the overall conversion yield that is increased by 1 to 3 percentage points—and at the same time guaranteeing a suitable protection of the reaction space against the corrosion.

In the same way as for the flow comprising ammonia and carbon dioxide in vapour phase, also in this case the term "major portion" is meant to indicate a portion greater than 50% of the overall flow of passivating agents coming out of the stripping unit.

For example, in case of a major portion comprised between 65–85% of the inert gas flow, only 15–35% of such inert gases is sent to the synthesis reactor, as compared to 100% for the prior art, with ensuing remarkable advantages in terms of greater conversion yield.

In this regard, it shall be noticed how it is praxis in the field to feed to the stripping unit a predetermined amount of passivating agents (for example, air or oxygen) together with the flow of carbon dioxide, in order to protect the apparatuses of the synthesis section of the urea plants—and in particular the stripping unit—from a fast deterioration due to the corrosive action of the substances involved in such reaction. Therefore, the passivating agents and other possible inert substances, which may be contained in the flow of carbon dioxide, pass through the condensation unit(s) and are then sent to the reactor for urea synthesis.

As the operative conditions are less critical than for the stripping unit, the amount of passivating agents theoretically required for protecting the condensation section and the reaction space is substantially lower than that effectively circulating in the synthesis loop.

Consequently, both the processes for urea production with stripping in carbon dioxide, and the methods of modernisation of the plants for urea production according to the prior art, are influenced by a loss of conversion yield in the reaction space and therefore of a missing production capacity due to the content in excess of inert substances in such reaction space.

Thanks to the present invention, the increase in conversion due to a smaller amount of inert substances present in the reaction space together with the conversion increase due to the increase of the previously described overall reaction volume, permits to maximise the increase of conversion yield in the reaction space and therefore of the production capacity of the existing plant, without creating in this way imbalances or disorders downstream the reaction space, and in particular overloads of the existing condensation section.

Further on, it is worth mentioning that with the aforesaid increases of conversion yield, it is advantageously possible to maintain the energy consumption low and even, in some instances, to reduce the steam consumption with respect to the existing plant to be modernised.

The major and minor portions of the flow comprising ammonia and carbon dioxide in vapour phase respectively of the gaseous flow comprising one or more passivating agents is preferably adjusted according to this method of modernisation thanks to the step of providing suitable controlling means in the means for extracting and feeding the major portion of the gaseous flow comprising one or more passivating agents together with possible traces of ammonia and carbon dioxide in vapour phase from the condensation unit to such washing unit.

According to a further aspect thereof, the present invention relates to a process for producing urea of the type comprising the steps of:

reacting ammonia and carbon dioxide in a reaction space, obtaining a reaction mixture comprising urea, carbamate and free ammonia in aqueous solution;

feeding the reaction mixture to a stripping section with carbon dioxide and subjecting the mixture to a treatment of partial decomposition of carbamate and partial separation of free ammonia, obtaining a flow comprising ammonia and carbon dioxide in vapour phase and a flow comprising urea and residual carbamate in aqueous solution;

feeding the flow comprising urea and residual carbamate in aqueous solution to an urea recovery section;

and which is characterised in that it further comprises the steps of:

feeding a minor portion of the flow comprising ammonia and carbon dioxide in vapour phase directly to the reaction space;

feeding a major portion of the flow comprising ammonia and carbon dioxide in vapour phase to at least one condensation unit and subjecting such major portion to a substantially total condensation, obtaining a flow comprising urea and carbamate in aqueous solution;

feeding the flow comprising urea and carbamate in liquid phase to the reaction space.

This invention further relates to a plant intended for carrying out the aforesaid process for producing urea, comprising:

a reactor for urea synthesis;

means for feeding ammonia and carbon dioxide to the reactor for urea synthesis;

a stripping unit with carbon dioxide for subjecting a reaction mixture comprising urea, carbamate and free ammonia in aqueous solution leaving the reactor to a treatment of partial decomposition of carbamate and partial separation of free ammonia, obtaining a flow comprising ammonia and carbon dioxide in vapour phase and a flow comprising urea and residual carbamate in aqueous solution;

a recovery section of the flow comprising urea and residual carbamate in aqueous solution leaving the stripping unit for separating urea from the residual carbamate in aqueous solution;

and which is characterised in that it further comprises:

at least one condensation unit of the "submerged" type for subjecting to substantially total condensation at least part of the flow comprising ammonia and carbon dioxide in vapour phase leaving the stripping unit, obtaining a flow comprising urea and carbamate in aqueous solution;

means for feeding a minor portion of the flow comprising ammonia and carbon dioxide in vapour phase leaving the stripping unit directly to the reactor for urea synthesis;

means for feeding a major portion of the flow comprising ammonia and carbon dioxide in vapour phase leaving the stripping unit to such at least one condensation unit;

means for feeding the flow comprising urea and carbamate in aqueous solution leaving said at least one condensation unit to the reactor for urea synthesis.

According to the invention, the plants intended for carrying out the process for urea production can be realised both ex-novo or by modifying pre-existing plants, so as to obtain an increase in the production capacity and in some cases an improved performance from the point of view of energy consumption.

Further features and advantages of the present invention will appear more clearly from the following non limiting description of an embodiment of the method of modernisation and of the urea synthesis process according to the invention, made with reference to the attached drawings.

DETAILED DESCRIPTION OF A PREFERRED EMBODIMENT

Figure 1:
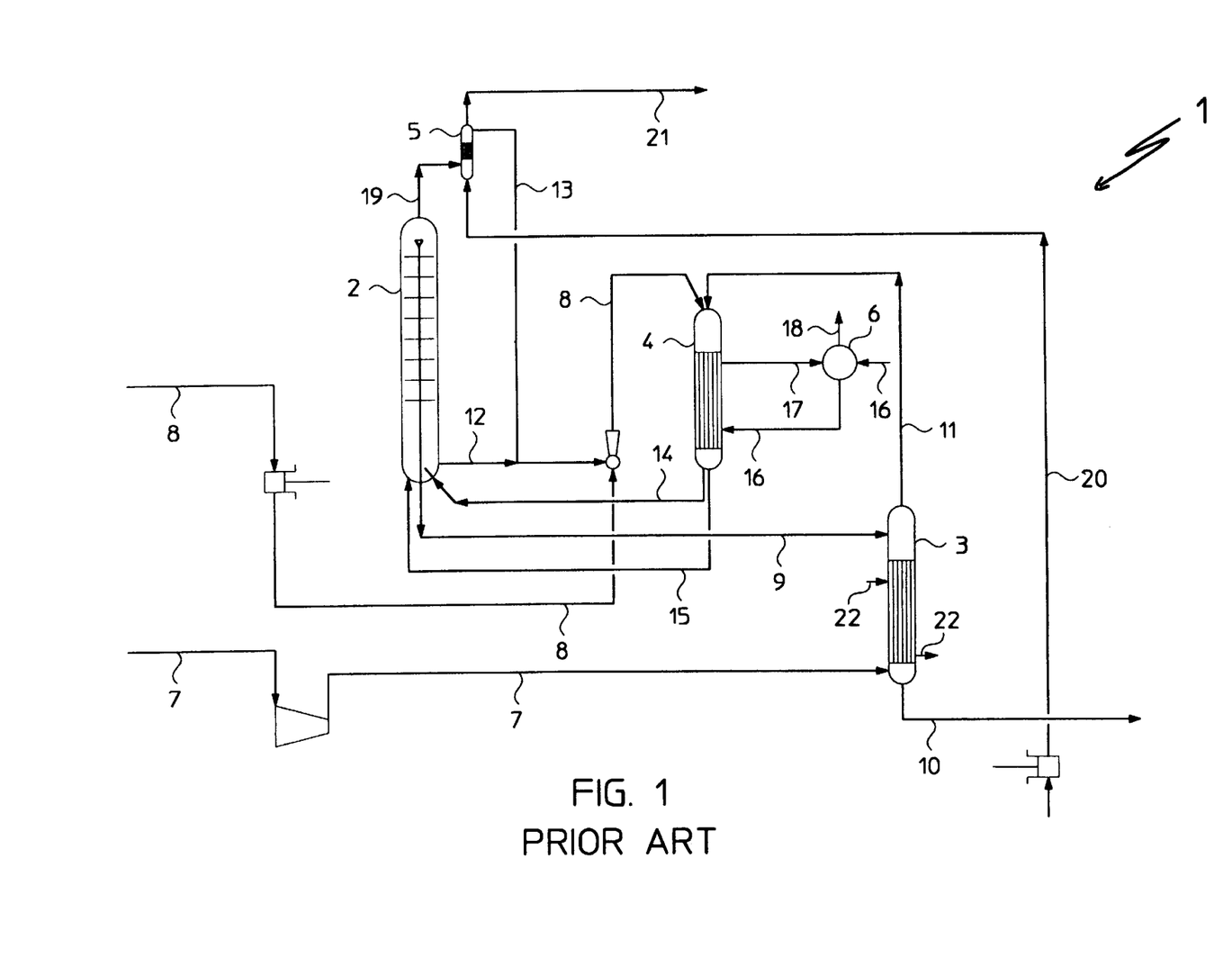
FIG. 1 illustrates schematically and partially a plant for urea production according to the stripping process with carbon dioxide of the prior art.

Just to simplify the disclosure of the present invention, only a portion of a plant for urea production is schematically represented in FIG. 1 and more precisely the high pressure synthesis section (synthesis loop), the remaining sections being not significant for the comprehension of the present invention.

Further on, specific reference to the per se conventional connecting ducts of the various parts of the plant described hereinbelow and illustrated in FIG. 1, will be made only when strictly necessary.

With reference to FIG. 1, an existing plant for urea production according to the stripping process with carbon dioxide and featuring the recycle of the reactants to the reaction space, is indicated in whole with reference numeral 1.

Plant 1, and more specifically the high pressure synthesis section, comprises a reactor 2 (or reaction space) for urea synthesis, a stripping unit 3 with carbon dioxide, a condensation section comprising a vertical condensation unit 4 of the film type, which will be described in greater detail with reference to FIG. 2, and a washing unit 5 of the passivating agents and other possible substances inert to the reaction.

Moreover, plant 1 comprises a recovery section for the urea produced, not represented in FIG. 1, and an apparatus 6 for the separation of the steam produced by the cooling liquid fed to the condensation unit 4.

The reactor 2 operates usually at a temperature comprised between 180 and 185° C. with a molar ratio $NH_3/CO_2$ comprised between 2, 8 and 3, 0, a molar ratio $H_2O/CO_2$ comprised between 0, 4 and 0, 5, and a conversion yield comprised between 58 and 60%.

The (isobaric) process pressure in the synthesis section of FIG. 1 is usually comprised between 140 and 145 bar. Such pressure is usually indicated in the urea synthesis processes as "high" pressure, as compared with the terms "medium" (about 18 bar) and "low" (3-4 bar) pressure, respectively, used in the field to indicate the pressure in the sections downstream the synthesis loop.

In FIG. 1, with the numerals 7–21 respective means for feeding the various flows to the apparatuses of plant 1 for urea production are generally indicated.

Such feeding means comprises pipelines or connecting ducts, pumps, compressors, ejectors and other devices of known type, generally employed in such kind of plants, and therefore they will not be further described in the following description.

Generally, in the present description and in the enclosed claims, and where it is not differently indicated, by the terms: "feeding, connecting or extraction means", it is intended to mean pipelines, connecting lines or ducts, pumps, compressor, ejectors or other devices of known type, which are used for transporting a liquid or gaseous flow from a location to another one in the plant.

More in particular, with 7 and 8 are indicated respective means for feeding to the stripping unit 3 a gaseous flow comprising feed carbon dioxide, and to the condensation unit 4 a flow comprising feed ammonia (in liquid phase).

The feed carbon dioxide sent to the stripping unit 3 through means 7 is employed as stripping agent of a reaction mixture comprising urea, carbamate and free ammonia in aqueous solution leaving the reactor 2 and fed to the unit 3 through means 9.

The stripping unit 3 is of the film type with an external heating with steam. Means for feeding and extracting steam for the heating of the stripping unit 3 on the shell side are generally indicated with 22.

The reaction mixture flowing downwards in the unit 3 in countercurrent with the gaseous flow comprising carbon dioxide is subjected to a treatment of partial decomposition of carbamate and partial separation of the free ammonia, obtaining a flow comprising ammonia and carbon dioxide in vapour phase and a flow comprising urea and residual carbamate in aqueous solution.

The flow comprising urea and residual carbamate in aqueous solution is extracted from the bottom of the stripping unit 3 and sent to the urea recovery section (non represented) through the feeding means 10.

The gaseous flow obtained in the stripping unit 3 and comprising also water in addition to ammonia and carbon dioxide, flows out from an upper end of such unit 3 and is fed to an upper end of the condensation unit 4 through feeding means 11.

The condensation unit 4 is of the vertical film type for subjecting to partial condensation all the flow comprising ammonia and carbon dioxide in vapour phase coming from the unit 3 through means 11.

Further on, the flow comprising feed ammonia is fed to the upper end of the condensation unit 4 through means 8 together with a recycled flow comprising ammonia and carbamate in aqueous solution. Recycled ammonia and carbamate in aqueous solution are fed into the flow comprising feed ammonia through feeding means 13. Connecting means 12 are also provided between the reactor 2 and the feeding means 13.

Figure 2:
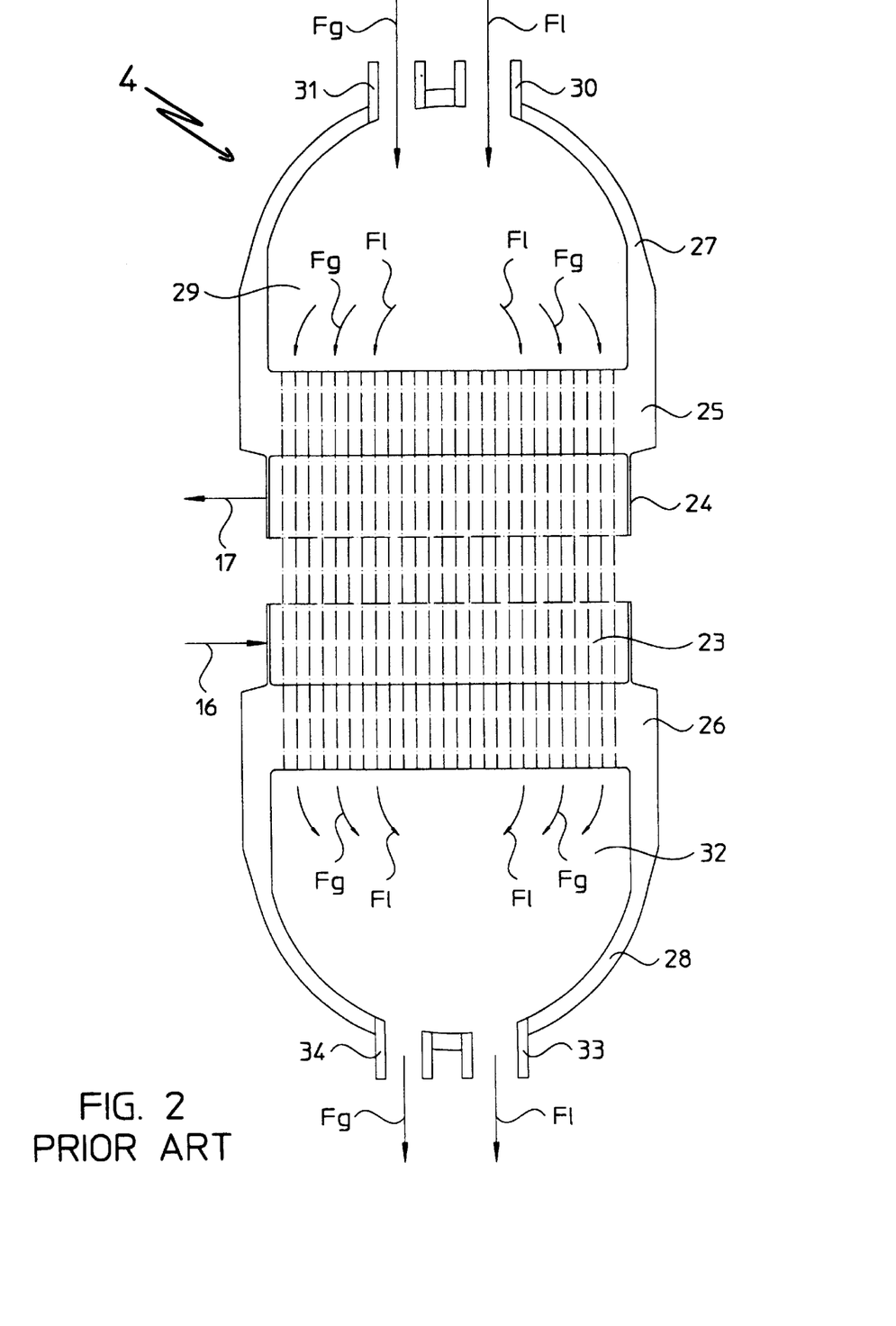
FIG. 2 shows a schematic view in longitudinal section of the vertical condensation unit of the film type of the plant of FIG. 1 according to the prior art.

As shown in FIG. 2, the partial condensation of the gaseous phase takes place as a result of the contact of such phase with the liquid phase, flowing in co-current downwards inside a plurality of tubes of a tube bundle 23 enclosed in a shell 24 of the condensation unit 4.

In such figure, details of plant 1 equivalent as for structure and operation to those of FIG. 1 will be indicated using the same reference numerals and will not be described any more.

The tube bundle 23 is delimited on its upper and lower part by tube plates 25 and 26 respectively, to which the upper and lower heads 27, 28, of the condensation unit 4 are respectively fixed.

In particular, the liquid phase comprising feed ammonia and recycled carbamate in aqueous solution is introduced through the inlet nozzle 30 in the space 29 defined by the upper head 27, spread on the upper tube plate 25 and made to fall by gravity along the tubes of the tube bundle 23 thus forming a film. Also the gaseous phase comprising ammonia and carbon dioxide fed to the upper tube plate 25 through the inlet nozzle 31 flows inside such tubes (which operates substantially empty).

As a consequence of the partial condensation, a liquid flow comprising carbamate in aqueous solution and a gaseous flow comprising ammonia and carbon dioxide in vapour are obtained at the tubes outlet of the tube bundle 23. Such flows pass through the space 32 defined inside the lower head 28 and flow out of the condensation unit 4 through the outlet nozzles 33, 34 for the liquid and for the gaseous phase, respectively.

The phase comprising ammonia and carbon dioxide in gaseous phase, as well as the phase comprising carbamate in aqueous solution are hence separately sent from the bottom of the condensation unit 4 to the reactor 2 for urea synthesis through respective feeding means 14, 15.

In FIG. 2, the flows of the gaseous phase and the liquid phase inside the condensation unit 4 are generally indicated with Fg and Fl, respectively.

It is clear that in the condensation unit 4 according to the prior art, the residence times of the phases inside the tubes of the tube bundle 23 are extremely low, as well as an uniform distribution of the liquid phase on the upper tube plate 26 can be rather difficult to be achieved. All this is detrimental for an effective condensation of the reactants in gaseous phase.

The heat produced during the partial condensation of the flow comprising ammonia and carbon dioxide in vapour phase inside the unit 4, is removed by making a cooling liquid, i.e. water, to flow through the tube bundle 23—on the shell side—producing recovery steam (generally at 4.5 absolute bar).

The water flow is fed on the shell side to the condensation unit 4 through means 16, and extracted from such unit through means 17.

The water flow coming out of the unit 4, and comprising also the steam produced by indirect heat exchange with the process fluids flowing inside the condensation unit 4 on the tubes side, is fed through means 17 to the apparatus 6 for the separation of the steam produced from the water. This water is thus recycled through means 16 to the condensation unit 4 on the shell side, whereas the steam is extracted from the separation apparatus 6 through means 18.

In the technical language of the field, the separation apparatus 6 is also indicated with the term "steam drum".

In order to protect the apparatuses of the high pressure synthesis section from corrosion, the plant 1 further comprises the possibility of flowing one or more passivating agents, for example oxygen or air, inert to urea synthesis reaction, through such devices.

To this end, means are generally provided for feeding a gaseous flow, comprising the passivating agents, to the stripping unit 3 and from such stripping unit to the urea synthesis reactor 2, passing through the condensation unit 4.

In the example of FIG. 1, the passivating agents are directly mixed with the gaseous flow comprising feed carbon dioxide, therefore the aforesaid means for feeding the gaseous flow comprising passivating agents corresponds to feeding means 7.

Since the operation conditions in the stripping unit 3 are the most critical from the corrosion point of view, such unit requires an amount of passivating agents substantially greater than that practically required for the passivation of the other apparatuses. Accordingly, beside the stripping unit 3, the other apparatuses of the synthesis section are fed with overabundant amounts of passivating agents.

Moreover, the gaseous flow comprising carbon dioxide fed to the stripping unit 3 through the means 7 contains a certain amount of other inert substances, for example 1–3% in volume, which, together with the passivating agents, pass through the various apparatuses of the high pressure synthesis section.

In particular, the amount of passivating and inert agents usually fed to the urea synthesis reactor 2 is such to reduce by some percentage points the conversion yield of carbon dioxide in urea with respect to the yield achievable with a lower contents of substances inert to the synthesis reaction.

The flow of inert substances passes through the urea synthesis reactor 2 entraining a part of the unreacted ammonia and carbon dioxide in vapour phase, and is thus fed through means 19 from an upper end of the reactor 2 to the washing unit 5.

In the washing unit 5, ammonia and carbon dioxide in vapour phase are condensed by means of a washing flow comprising—in the example of FIG. 1—carbamate in aqueous solution coming from the urea recovery section (not represented) and fed to the unit 5 through means 20.

From the washing unit 5, the extraction of the passivating agents and of the inert substances in general from the high pressure synthesis section takes place through means 21, whereas the washing flow suitably enriched in ammonia and carbon dioxide is sent to the condensation unit 4 through means 13.

Figure 3:
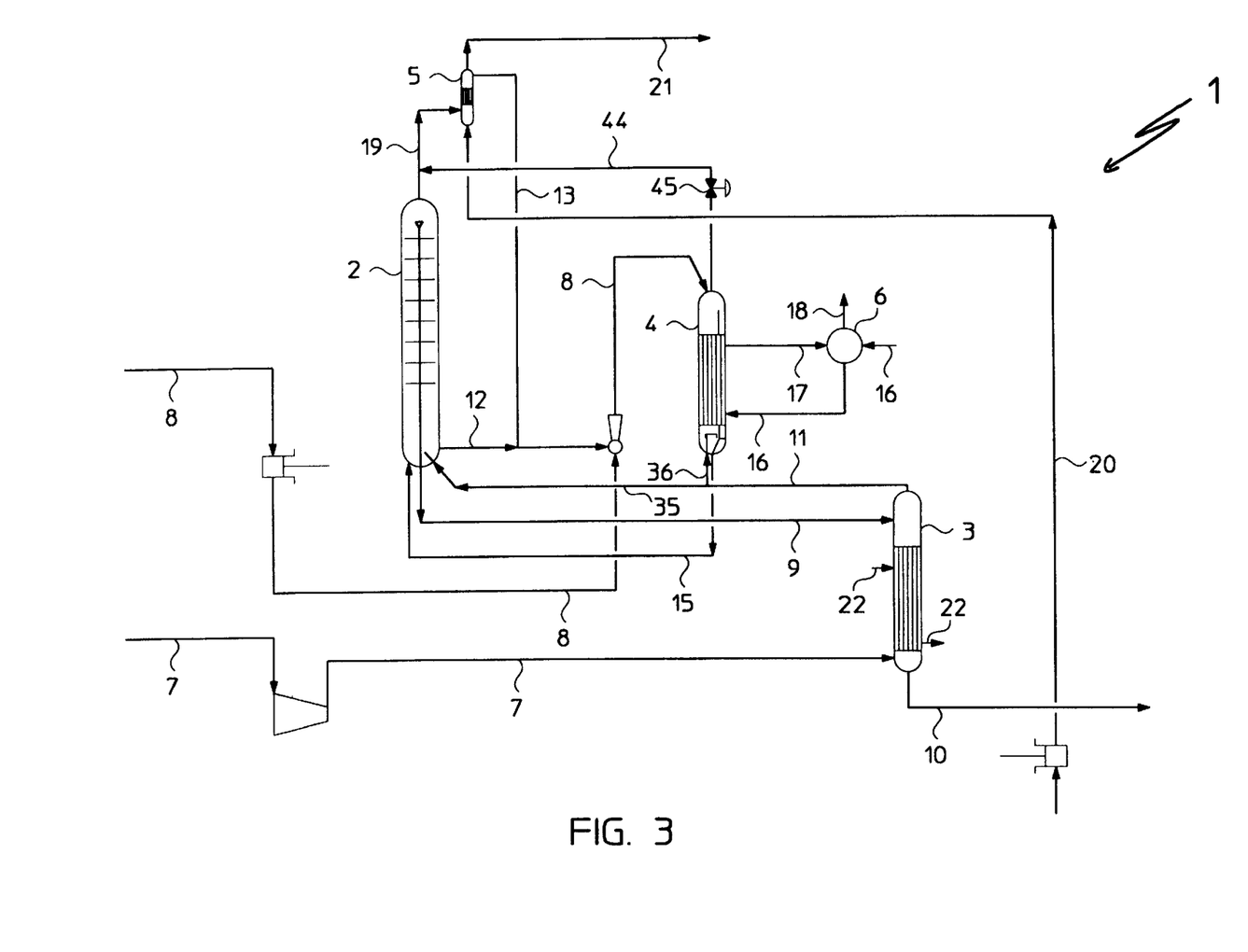
FIG. 3 illustrates schematically and partially a plant for urea production according to the stripping process with carbon dioxide realised by the modernisation of the plant of FIG. 1 in accordance with a preferred embodiment of the method of modernisation according to the invention.

With reference to FIG. 3, the plant for urea production of FIG. 1 is advantageously represented suitably modified according to a first embodiment of the method of modernisation of the present invention.

Figure 4:
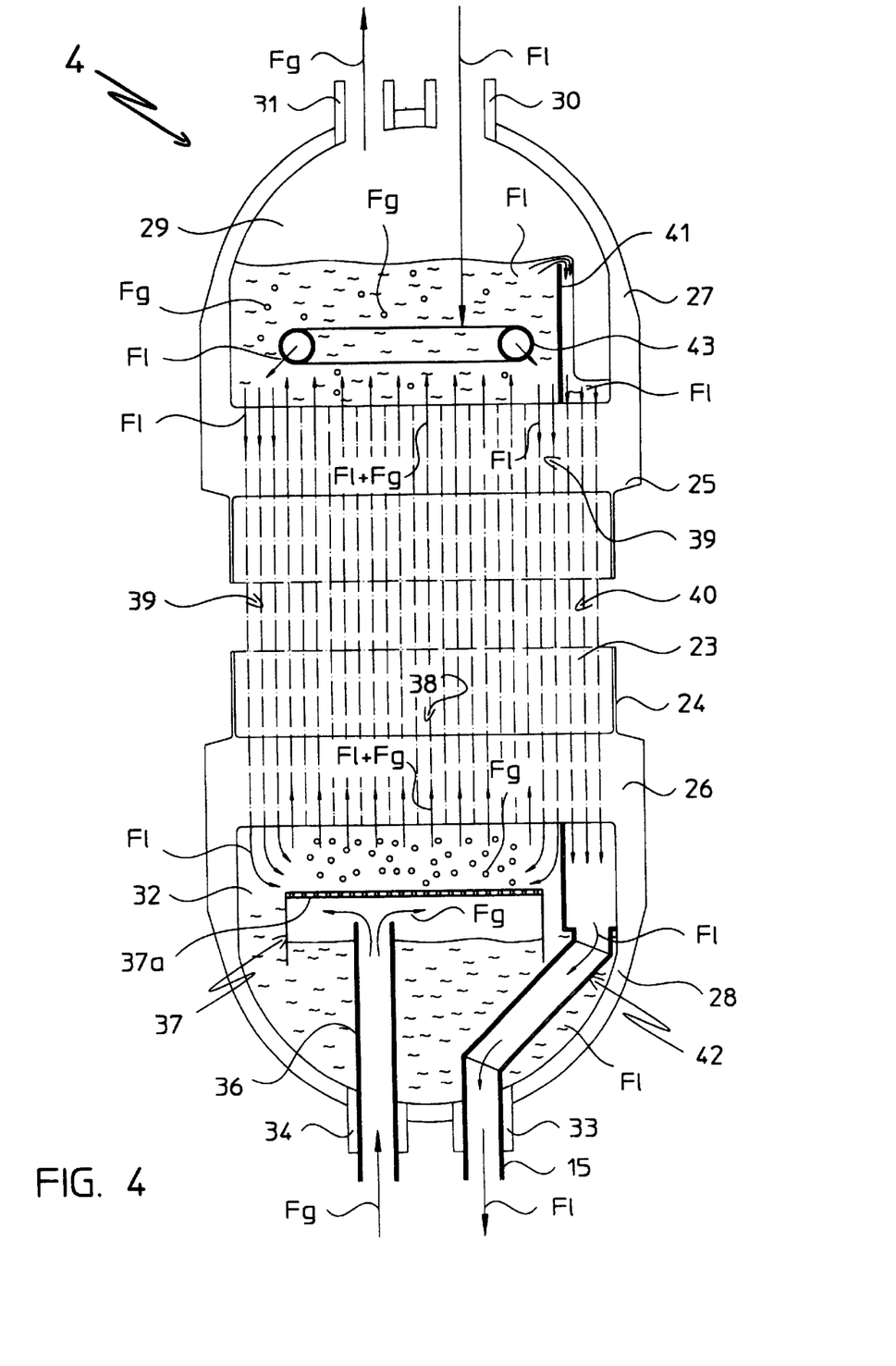
FIG. 4 shows a schematic view in longitudinal section of the vertical condensation unit of the "submerged" type of the plant of FIG. 3, obtained by modifying the condensation unit of FIG. 2 according to the present invention.

The particulars related to the modifications brought into the existing condensation unit, are better highlighted with reference to FIG. 4.

In FIGS. 3 and 4, the details of plant 1 and of the condensation unit 4 equivalent as for structure and operation to those illustrated in FIGS. 1 and 2, will be indicated with the same reference numerals and will not be described again.

Thanks to the present method of modernisation, the feeding means to the condensation unit 4 of the flow comprising ammonia and carbon dioxide in vapour phase coming out of the stripping unit 3 are suitably modified in such a way to subject only a major portion of such flow to condensation with the liquid phase.

Further on, the condensation unit 4 is advantageously modified in its internal so as to permit a substantially total condensation of such major portion.

To this end, according to the embodiment of FIG. 3, means 11 of the existing plant of FIG. 1 are modified and means 35 and 36 are provided for feeding a minor portion of the flow comprising ammonia and carbon dioxide in vapour phase from the stripping unit 3 directly to the urea synthesis reactor 2, and for feeding a major portion of such flow to the condensation unit 4, respectively. Means 35 and 36 comprises for examples respective connection ducts.

It is clear that, by making the gaseous flow comprising one or more passivating agents to flow inside the feeding means 11 together with the flow comprising ammonia and carbon dioxide in vapour phase, the provision of means 36 and 35 inevitably causes a corresponding separation in a minor and a major portion of the passivating agents fed to the reactor 2 and to the condensation unit 4, respectively.

Inside the condensation unit 4, means are provided, which are described in more detail in FIG. 4, for allowing condensation of substantially all the reactants in gaseous phase fed thereto in a simple and effective way.

In other words, the existing vertical condensation unit of the film type is advantageously transformed into a vertical condensation unit of the "submerged" type, i.e. with the tube bundle full of condensation liquid, remarkably improving the efficiency of such unit and thus its capacity. Moreover, this change allows to increase the residence time of formation carbamate in the condensation unit 4, which partially reacts in urea.

In particular, the condensation liquid comprising carbamate in aqueous solution and ammonia is advantageously made to circulate inside the tube bundle 23 with a termosiphon like motion. The major portion of the flow comprising ammonia and carbon dioxide in vapour phase is instead fed through means 36 into the lower space 32 near a lower end of the tube bundle 23, and more precisely proximate to the lower tube plate 26.

In doing so, ammonia and carbon dioxide in vapour phase pass through the condensation unit 4 upwards—in co-current with the condensation liquid—gurgling inside the tubes full of liquid of the tube bundle 23 and thus with a considerable exchange coefficient on the tubes side.

In order to allow a correct circulation with a termosiphon like motion of the condensation liquid inside the condensation unit 4, the present method of modernisation comprises the provision of a gas distributor 37 comprising a perforated wall 37a provided proximate to the lower tube plate 26 in fluid communication with the feeding means 36 of the major portion of the flow comprising ammonia and carbon dioxide in vapour phase.

The distributor 37 is dimensioned in such a way to distribute advantageously the ammonia and carbon dioxide in vapour phase only in a determined portion of the tube bundle 23.

In this way, the tube bundle 23 is inherently subdivided in a first portion 38 (a central portion in FIG. 4) through which a low specific weight liquid/gaseous flow passes upwards, and in a second portion 39 (a peripheral portion in FIG. 4) through which only the high specific weight liquid flow passes downwards, which circulates therefore in a thermosiphon like motion inside the condensation unit 4.

As illustrated in FIG. 4, a further peripheral portion 40 of the tube bundle 23 is used for the passage from the upper space 29 to the feeding means 15 of the flow comprising urea and carbamate in aqueous solution to be sent to the synthesis reactor 2.

In this respect, the method of modernisation according to the invention provides that suitable means, indicated in FIG. 4 with 41 and 42, be provided inside the condensation unit 4 for collecting and feeding such flow comprising urea and carbamate in aqueous solution from the space 29 to the means 15 through the third portion 40 of the tube bundle 23.

Such collecting and feeding means comprise a wall 41 which is not perforated and extends vertically from the upper tube plate 25 for a portion of the upper space 29, and connecting means 42 between the portion of the lower tube plate 26 which receive the flow comprising urea and carbamate in aqueous solution to be sent to the reactor 2 and the feeding means 15.

The wall 41 defines a liquid head in the upper space 29 of the liquid phase circulating according to a thermosiphon like motion and separates as weir the flow comprising urea and carbamate in aqueous solution to be sent to means 42 through the portion 40 of the tube bundle 23.

It shall be noted how, increasing the height of the wall 41 and therefore the level of the liquid phase in the space 29, it is possible to increase the residence time of such phase in the condensation unit 4 to full advantage of a higher production rate of urea in such unit.

In turn, means 42 may for example comprise a box-shaped device fixed to the lower tube plate 26 for collecting the liquid phase coming from the portion 40 of the tube bundle 23, and connected to means 15 through a duct passing through the nozzle 33.

The flow of condensation liquid comprising carbamate in aqueous solution and ammonia fed to the condensation unit 4 through means 8 leads into the upper space 29 through the inlet nozzle 30 and is distributed through a toroidal distributor 43 proximate to the upper tube plate 25 in the portion 39 of the tube bundle 23.

The passivating agents and other possible inert substances for the urea synthesis reaction fed to the condensation unit 4 through means 34 pass through the tube bundles 23 upwards and separate from the liquid phase in the upper space 29 of unit 4 together with possible uncondensed traces of ammonia and carbon dioxide in vapour phase.

Advantageously, the gaseous phase that separates from the liquid phase in the upper space 29 is extracted from the condensation unit 4 and fed to the washing unit 5 downstream the reactor 2 thanks to the provision—according to the present method of modernisation—of suitable means 44.

Such means 44, for example, consist of a duct in fluid communication with the upper space 29 of the condensation unit 4 through the nozzle 31.

As seen with reference to the summary of the invention, thanks to this feature it is possible to increase the conversion yield in the urea synthesis reactor 2 by some percentage point (1–3%) with considerable advantages as far as an increase of the production capacity of the existing plant is concerned.

In doing so, not only the conversion yield is increased, but the reactor 2 may operate in more favourable conditions and the plant energy consumption are lower than before the modernisation (lower steam consumption).

A further advantage resulting from this embodiment of the present method of modernisation consists in that, feeding to the synthesis reactor 2 exclusively a minor portion of the inert substances, the amount of ammonia and carbon dioxide in vapour phase leaving the reactor 2 will be remarkably lower than when all inert substances are fed to the reactor 2.

Accordingly, as the major portion of the inert substances coming from the condensation unit 4 contains only traces of ammonia and carbon dioxide, a decrease of the load of the washing unit 5 is further obtained; hence, this unit will have to recover smaller amounts of reactants in gaseous phase (to separate from the flow of inert substances smaller amounts of ammonia and carbon dioxide in vapour phase), allowing better operation conditions of unit 5 and therefore an increase in the capacity of such unit.

According to further embodiments (not shown), it is foreseen to provide means for feeding the flow of inert substances coming from the condensation section 4 to other washing units downstream of the reactor 2, which are present in the existing plant for urea production. Alternatively, whenever the content of ammonia and carbon dioxide in the flow of inert substances coming out of the unit 4 is null or substantially null, it is possible to foresee the step of providing means (not shown) for evacuating such flow immediately into the environment, for example a vent valve connected to the gas outlet nozzle 31.

Preferably, according to the present method of modernisation, it is foreseen to provide, in means 44, suitable means 45, illustrated in FIG. 3 by a control valve, for the control of the major and minor portion of the gaseous flow comprising ammonia and carbon dioxide in vapour phase, respectively of the gaseous flow comprising one or more passivating agents.

As the means 44 put in fluid communication the top of the condensation unit 4 with the top of reactor 2, the control valve 45 permits to control the amount of ammonia and carbon dioxide in vapour phase to be sent to the condensation unit 4, respectively to the urea synthesis reactor 2.

Depending on the size and specific geometry of the tube bundle 23, the present invention provides a method of modernisation that allows to further increase the overall exchange coefficient of the condensation unit 4, increasing the heat exchange coefficient outside of the tube bundle 23 (shell side) where the cooling water is made to flow, in addition to the increase inside the tubes (tube side) where the process flows pass, to full advantage of the condensation unit capacity which is thereby improved.

It has been surprisingly found that in order to ameliorate the removal of heat produced during the condensation of ammonia and carbon dioxide in vapour phase and therefore to increase the heat exchange coefficient, it is preferable not to generate steam during the crossing on the shell side of the tube bundle 23 by the cooling water.

In fact, in the specific case wherein the tube bundle 23 of the existing condensation unit 4 has a very high number of tubes provided close to each other and the space available for the passage of water on the shell side is small, the presence of steam of formation in the cooling water flowing on the shell side in the condensation unit 4 seems to be detrimental for the circulation of the liquid. This would imply a decrease in the heat exchange and accordingly a reduced removal of condensation heat between the flows flowing on the tube side and the cooling water.

It is worth noting that this feature is well in contrast with the teaching of the prior art, wherein evaporation of the cooling water for the removal of condensation heat is carried out during the crossing on the shell side of the tube bundle, with the purpose of promoting the heat removal and having a good exchange coefficient on the shell side.

Therefore, in the specific cases of condensation units with a high number of tubes arranged close to each other, the present invention provides advantageously the arrangement of suitable means for increasing the flow rate of the cooling water in such a way to prevent the formation of steam inside the condensation unit 4 and further increase the overall heat exchange coefficient.

The increase of the flow rate and hence of the circulation of water inside the cooling loop is obtained, for example, through the arrangement of a ricirculation pump (not shown) in the means 16 or, alternatively, by increasing the height of the apparatus 6, i.e. increasing the difference in height between the apparatus 6 and the unit 4 so as to increase the liquid head.

In doing so, the inlet pressure at the shell side of unit 4 increases and the temperature increase becomes smaller so that steam is formed only at the outlet of such unit 4.

Thanks to these modifications of the cooling loop, high exchange coefficients on the shell side may be attained, even in those specific cases wherein the condensation unit has a tube bundle with the above mentioned characteristics.

In general, the method of modernisation according to the present invention allows not only to increase the capacity of the condensation unit 4 but also to obtain an increase of the pressure of the steam produced, and therefore a heat recovery at a higher thermal level.

The steam at higher pressure so obtained may advantageously be used in other parts of the plant 1 for urea production, for example in the heat exchangers downstream the synthesis section or in the $CO_2$ compressor turbine, reducing the loads and the energy consumption of such apparatuses.

Figure 5:
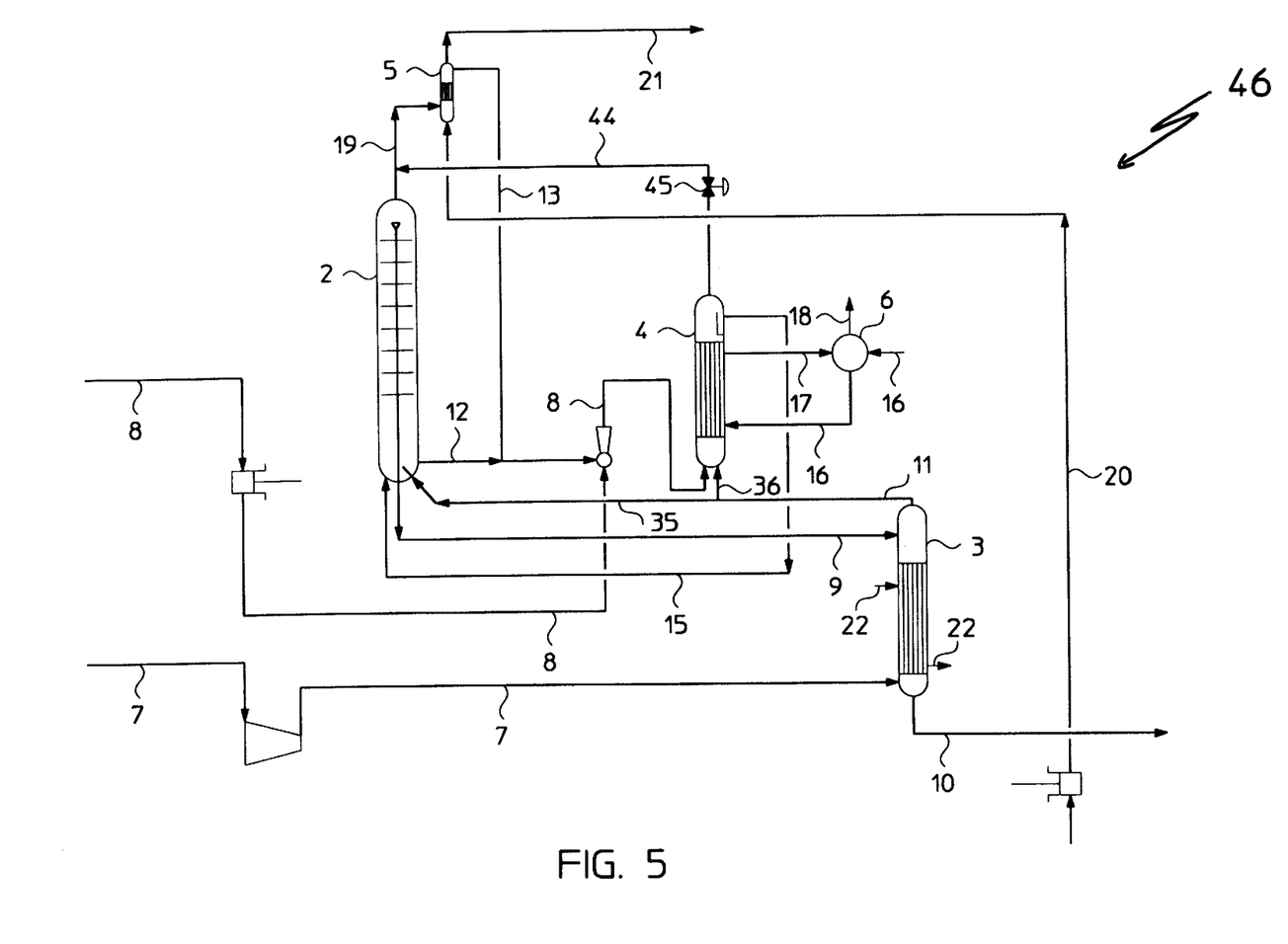
FIG. 5 illustrates schematically and partially a plant for urea production according to the stripping process with carbon dioxide realised ex-novo for carrying out the process according to the invention.

With reference to FIG. 5, a plant 46 for urea production according to the stripping process with carbon dioxide is advantageously represented, realised ex-novo for carrying out the process according to the invention.

Figure 6:
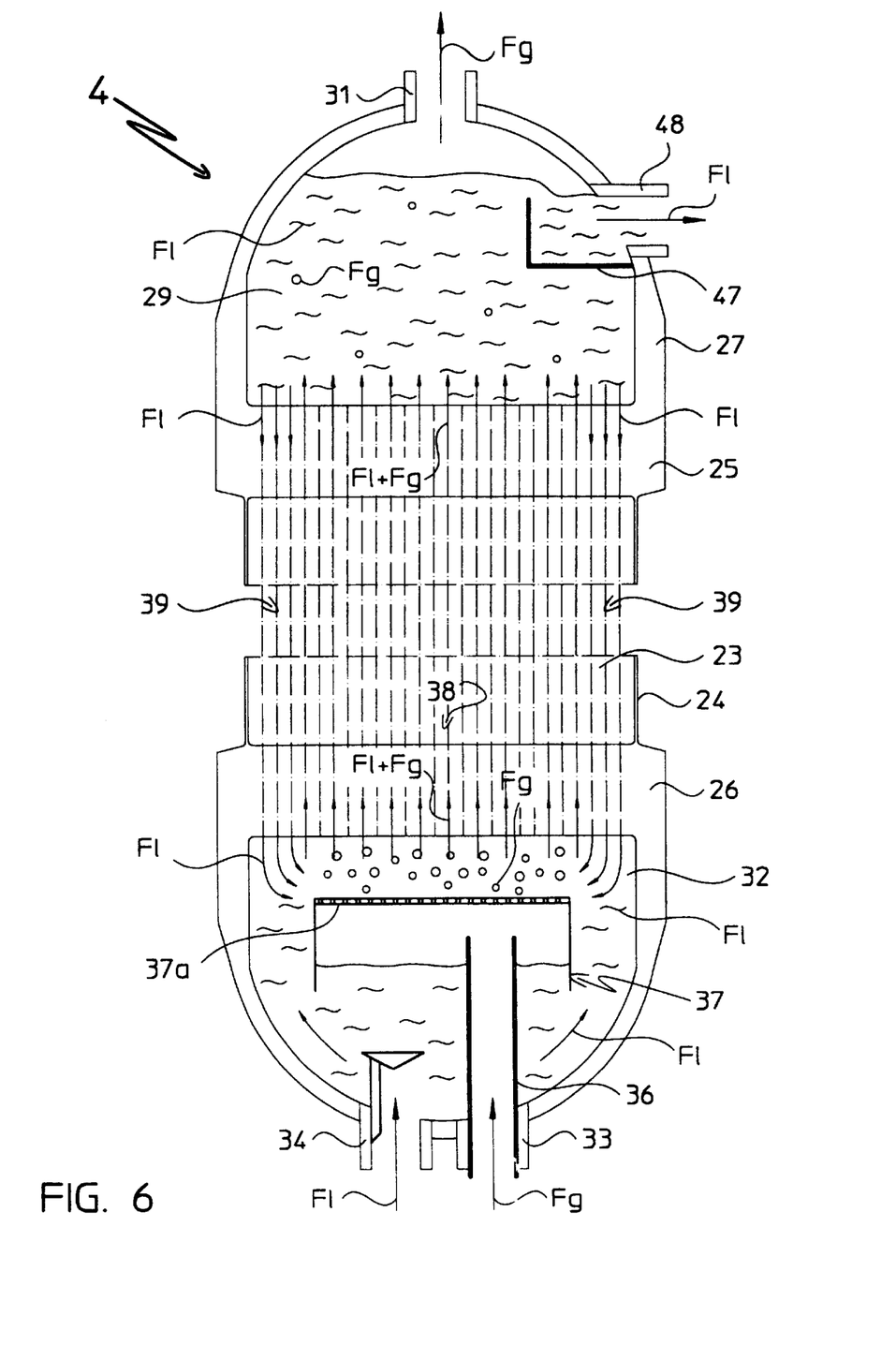
FIG. 6 shows a schematic view in longitudinal section of the vertical condensation unit of the "submerged" type of the plant of FIG. 5 according to the present invention.

The particulars related to the condensation unit 4 of the new plant are better shown in FIG. 6.

In FIGS. 5 and 6, the details of the plant 46 and of the condensation unit 4 which are structurally and functionally equivalent to those illustrated in the preceding figures will be indicated with the same reference numerals and will not be further.

In other words, as far as the description of the various means and apparatuses of plant 46, as well as the description of its operation is concerned, reference is substantially made to FIGS. 3 and 4.

The only relevant difference is given by the different inlet into the unit 4 of the flow comprising ammonia and carbamate in aqueous solution (means 8) and by the different outlet from such unit of the flow comprising urea and carbamate in aqueous solution to be sent to the reactor 2 (means 15).

These differences are due to the fact that, as the construction of a new condensation unit was possible, the arrangement of the inlet and outlet nozzles for the various streams was optimised.

In this way, the presence of collecting and feeding means 41, 42, in the upper and lower spaces 29 and 30, respectively, is avoided. Further on, it is avoided to use a part of the tube bundle 23 for the extraction of the flow comprising urea and carbamate in aqueous solution from the condensation unit 4. Therefore, it is obtained a maximum exploitation of the inner volume of the unit 4 available for the condensation of ammonia and carbon dioxide in vapour phase.

In particular, the phase comprising ammonia and carbamate in aqueous solution is now fed—through means 8—to the unit 4 through the nozzle 34 arranged at the bottom of such unit. Moreover, the flow comprising urea and carbamate in aqueous solution to be fed to the reactor 2 through means 15, leaves the unit 4 through a nozzle 48 arranged proximate to its upper end.

In order to secure a constant flow of liquid leaving the nozzle 48, the upper collection chamber 29 is further provided with a collection vessel 47 that operates as collector of the liquid phase to be supplied to the reactor 2.

The scheme of FIG. 5 represents anyway only a preferred embodiment of a new plant for urea production according to the present invention. In fact, nothing prevents new plants to be realised in an advantageous way according to the scheme of FIG. 3.

The advantages described with reference to the modernisation of existing plants recur in the plant realised ex-novo of FIG. 5, with the exception of the investment costs that are, of course, much higher for a new plant.

Thanks to the plant of FIG. 3 obtained after the modernisation of an existing plant and to the new plant of FIG. 5, it is advantageously possible to carry out the process for urea production described and claimed in the enclosed claims 9–13.

In particular, such process is characterised in that it comprises the steps of feeding (means 35) a minor portion of the flow comprising ammonia and carbon dioxide in vapour phase directly to the reaction space 2, of feeding (means 36) a major portion of the flow comprising ammonia and carbon dioxide in vapour phase to at least one condensation unit 4 and subjecting this major portion to substantially total condensation thus obtaining a flow comprising urea and carbamate in aqueous solution, of feeding (means 15) the flow comprising urea and carbamate in aqueous solution to the reaction space 2.

Preferably, in order to promote the above mentioned substantially total condensation of the major portion of the gaseous phase fed to the condensation unit 4, the process according to the invention comprises the step of flowing such major portion in the condensation unit 4 through a flow of liquid comprising carbamate in aqueous solution and ammonia circulating inside such unit in a thermosiphon-like motion.

Still more precisely, the process comprises the step of flowing the major portion of the flow comprising ammonia and carbon dioxide in vapour phase together with the flow of liquid comprising carbamate in aqueous solution and ammonia upwards inside a preferably central, predetermined portion 38 of a vertical tube bundle 23 of the condensation unit 4.

According to a preferred embodiment of the present invention, the process comprises advantageously the steps of extracting and feeding (means 44) the major portion of the gaseous flow comprising one or more passivating agents together with possible traces of ammonia and carbon dioxide in vapour phase from the condensation unit 4 to a washing unit 5 downstream of the reaction space 2, for the recovery of the traces of ammonia and carbon dioxide with a washing flow, preferably a flow comprising carbamate in aqueous solution coming from the recovery section for urea.

Further on, in some specific cases, it may be advantageous to feed the flow comprising cooling water (means 16) to the condensation unit 4 (on the shell side) with such a flow rate so as to limit at least partially the formation of steam inside said unit 4.

The advantages attained with the process according to the present invention are various. In particular it is worth stressing that such process allows to obtain—simply and effectively—a high exchange coefficient in the condensation unit 4, high conversion yields and therefore high production capacity. Further on, its realisation is technically easy, with low energy consumption and investment costs.

Finally, the scope of protection defined by the method of modernisation according to the present invention shall be considered as being extended—beside the modification of existing structures—also to the particular case of a replacement—because of wear—of the existing condensation unit with a new unit having a configuration of the kind represented in FIGS. 4 and 6. This specific case occurs whenever the existing unit is at the end of its operating life and does not guarantee a reliable and lasting operation any more.

What is claimed is:

1. Method for the modernisation of a plant for urea production comprising:

a reactor (2) for urea synthesis;

means (7, 8) for feeding ammonia and carbon dioxide to said reactor (2) for urea synthesis;

a stripping unit (3) with carbon dioxide for subjecting a reaction mixture comprising urea, carbamate and free ammonia in aqueous solution leaving said reactor (2) to a treatment of partial decomposition of carbamate and partial separation of free ammonia, thus obtaining a flow comprising ammonia and carbon dioxide in vapour phase and a flow comprising urea and residual carbamate in aqueous solution, respectively;

a recovery section for said flow comprising urea and residual carbamate in aqueous solution leaving said stripping unit (3) for separating the urea from the residual carbamate in aqueous solution;

at least one vertical film condensation unit (4), comprising a tube bundle (23) for subjecting to partial condensation said flow comprising ammonia and carbon dioxide in vapour phase leaving said stripping unit (3), thus obtaining a liquid flow comprising carbamate in aqueous solution and a gaseous flow comprising ammonia and carbon dioxide in vapour phase;

means (15, 14) for respectively feeding the flow comprising carbamate in aqueous solution and the gaseous flow comprising ammonia and carbon dioxide in vapour phase to said reactor (2) for urea synthesis;

means (7, 11, 14) for feeding a gaseous flow comprising one or more passivating agents, inert with respect to the synthesis reaction of urea, to said stripping unit (3) and from the stripping unit (3) to said reactor (2) for urea synthesis through said at least one condensation unit (4);

said modernisation method being characterised in that it comprises the steps of:

providing means (35) for feeding a minor portion of said flow comprising ammonia and carbon dioxide in vapour phase together with a minor portion of said gaseous flow comprising one or more passivating agents leaving said stripping unit (3) directly to said reactor (2) for urea synthesis;

providing means (36) for feeding a major portion of said flow comprising ammonia and carbon dioxide in vapour phase together with a major portion of said gaseous flow comprising one or more passivating agents leaving said stripping unit (3) to said at least one condensation unit (4);

providing in said at least one condensation unit (4) means (37) for subjecting to substantially total condensation said major portion of the flow comprising ammonia and carbon dioxide in vapour phase, obtaining a flow comprising urea and carbamate in aqueous solution.

2. Method according to claim 1, characterised in that it provides means (17) for transforming said at least one vertical film condensation unit (4) into a vertical submerged condensation unit.

3. Method according to claim 2, characterised in that said method provides means (36, 37) for feeding the major portion of said flow comprising ammonia and carbon dioxide in vapour phase in a lower end (26) of the tube bundle (23) of said at least one condensation unit (4) and means (37a) for circulating a condensation liquid flow comprising carbamate in aqueous solution and ammonia inside the condensation unit with a natural motion.

4. Method according to claim 3, characterised in that said method provides a gas distributor (37, 37a) proximate to said lower end (26) of the tube bundle (23) in fluid communication with said means (36) for feeding the major portion of the flow comprising ammonia and carbon dioxide in vapour phase, to distribute ammonia and carbon dioxide in vapour phase in a preferably central, predetermined portion (38) of the tube bundle (23).

5. Method according to claim 2, characterised in that said method provides in said at least one condensation unit (4) means (41, 42) for collecting and feeding said flow comprising urea and carbamate in aqueous solution from an area (29) located above said tube bundle (23) to a lower end of said at least one condensation unit (4) in fluid communication with said means (15) for feeding the liquid phase to the reactor (2) for urea synthesis.

6. Method according to claim 1, characterised in that said method further comprises the step of:

providing means (44) for extracting and feeding said major portion of the gaseous flow comprising one or more passivating agents together with possible traces of ammonia and carbon dioxide in vapour phase from said at least one condensation unit (4) to a washing unit (5) provided downstream from said reactor (2) for urea synthesis.

7. Method according to claim 6, characterised in that said method further comprises the step of:

providing suitable means (45) for controlling the major and minor portions of said flow comprising ammonia and carbon dioxide in vapour phase and of said gaseous flow comprising one or more passivating agents respectively, in said means (44) for extracting and feeding said major portion of gaseous flow comprising one or more passivating agents together with possible traces of ammonia and carbon dioxide in vapour phase from said at least one condensation unit (4) to said washing unit (5).

8. Method of modernisation according to claim 1, characterised in that said method further comprises the step of:

providing means for increasing the flow rate of a flow comprising cooling water fed to said at least one condensation unit (4).

9. Plant for urea production, comprising:

a reactor (2) for urea synthesis;

means (7, 8) for feeding ammonia and carbon dioxide to said reactor (2) for urea synthesis;

a stripping unit (3) with carbon dioxide for subjecting a reaction mixture comprising urea, carbamate and free ammonia in aqueous solution leaving said reactor (2) to a treatment of partial decomposition of carbamate and partial separation of free ammonia, obtaining a flow comprising ammonia and carbon dioxide in vapour phase and a flow comprising urea and residual carbamate in aqueous solution;

a recovery section of said flow comprising urea and residual carbamate in aqueous solution leaving said stripping unit (3) for separating urea from the residual carbamate in aqueous solution; characterised in that it further comprises:

at least one submerged condensation unit (4) for subjecting to substantially total condensation at least part of said flow comprising ammonia and carbon dioxide in vapour phase leaving said stripping unit (3), obtaining a flow comprising urea and carbamate in aqueous solution;

means (35) for feeding a minor portion of said flow comprising ammonia and carbon dioxide in vapour phase leaving said stripping unit (3) directly to said reactor (2) for urea synthesis;

means (36) for feeding a major portion of said flow comprising ammonia and carbon dioxide in vapour phase leaving said stripping unit (3) to said at least one condensation unit (4);

means (15) for feeding said flow comprising urea and carbamate in aqueous solution leaving said at least one condensation unit (4) to said reactor (2) for urea synthesis.

10. Plant according to claim 9 characterised in that said at least one condensation unit (4) is vertical and comprises inlet nozzles (33, 34) for feeding said major portion of the flow comprising ammonia and carbon dioxide in vapour phase and for feeding a condensation liquid flow comprising carbamate in aqueous solution and ammonia respectively, arranged in a lower end thereof, and an outlet nozzle (48) of said flow comprising urea and carbamate in aqueous solution arranged proximate to an upper end thereof.

11. Plant according to claim 10 characterised in that said at least one condensation unit (4) comprises a tube bundle (23) and a gas distributor (37, 37a) proximate to a lower end (26) of the tube bundle (23) in fluid communication with said means (33) for feeding the major portion of the flow comprising ammonia and carbon dioxide in vapour phase, to distribute the ammonia and carbon dioxide in vapour phase in a preferably central, predetermined portion (38) of the tube bundle (23).

12. Plant according to claim 11, characterised in that it further comprises:
   - means (7) for feeding a gaseous flow comprising one or more passivating agents, inert to the urea synthesis reaction to said stripping unit (3);
   - means (35) for feeding a minor portion of said gaseous flow comprising one or more passivating agents from said stripping unit (3) directly to said reactor (2) for urea synthesis;
   - means (36) for feeding a major portion of said gaseous flow comprising one or more passivating agents from said stripping unit (3) to said at least one condensation unit (4);
   - means (44) for extracting and feeding said major portion of the gaseous flow comprising one or more passivating agents together with possible traces of ammonia and carbon dioxide in vapour phase from said at least one condensation unit (4) to a washing unit (5) arranged downstream of said reactor (2) for urea synthesis.

13. Plant according to claim 12, characterised in that it further comprises suitable means (45) for regulating the major and minor portion of said flow comprising ammonia and carbon dioxide in vapour phase and said gaseous flow comprising one or more passivating agents respectively, arranged in said means (44) for feeding the gaseous flows so extracted to said washing unit (5).

14. Plant according to claim 12, characterised in that said at least one condensation unit (4) comprises a nozzle (31) for extracting said major portion of the gaseous flow comprising one or more passivating agents together with possible traces of ammonia and carbon dioxide in vapour phase arranged in its upper end.

\* \* \* \* \*